United States Patent
Figlerowicz et al.

(10) Patent No.: US 9,051,559 B2
(45) Date of Patent: Jun. 9, 2015

(54) PEPTIDE WITH THE ENZYMATIC ACTIVITY OF A DICER-LIKE PROTEIN, A METHOD FOR PREPARING SHORT RNA MOLECULES, AND USE THEREOF

(75) Inventors: Marek Figlerowicz, Borowiec (PL); Aleksander Tworak, Poznan (PL); Jan Podkowinski, Poznan (PL); Natalia Koralewska, Rogowo (PL); Anna Kurzynska-Kokorniak, Poznan (PL)

(73) Assignee: INSTYTUT CHEMI BIOORGANICZNEJ PAN, Poznan (PL)

( * ) Notice: Subject to any disclaimer, the term of this patent is extended or adjusted under 35 U.S.C. 154(b) by 0 days.

(21) Appl. No.: 14/127,582

(22) PCT Filed: Jun. 25, 2012

(86) PCT No.: PCT/PL2012/000049
§ 371 (c)(1),
(2), (4) Date: Dec. 19, 2013

(87) PCT Pub. No.: WO2013/006069
PCT Pub. Date: Jan. 10, 2013

(65) Prior Publication Data
US 2014/0186895 A1 Jul. 3, 2014

(30) Foreign Application Priority Data
Jul. 1, 2011 (PL) .................................. 395495

(51) Int. Cl.
*C12N 9/22* (2006.01)
*C12N 15/82* (2006.01)
*C12P 19/34* (2006.01)

(52) U.S. Cl.
CPC .............. *C12N 9/22* (2013.01); *C12N 15/8218* (2013.01); *C12P 19/34* (2013.01)

(58) Field of Classification Search
None
See application file for complete search history.

(56) References Cited

U.S. PATENT DOCUMENTS

2010/0058490 A1  3/2010  Waterhouse et al.

FOREIGN PATENT DOCUMENTS

| WO | 2007128052 A1 | 11/2007 |
| WO | WO 2009/099580 A2 * | 8/2009 |
| WO | 2009117513 A2 | 9/2009 |

OTHER PUBLICATIONS

Slotte et al., "The *Capsella rubella* genome and the genomic consequences of rapid mating system evolution", Nature Genetics, Jul. 2013, vol. 45(7):831-835.*
Young et al., "The *Medicago* genome provides insight into the evolution of rhizobial symbioses", Nature, Dec. 2011, 480(22/29):520-524.*
Macrae et al., "Structural basis for double-stranded RNA processing by dicer", Science, Jan. 13, 2006, pp. 195-198, vol. 311, Nr: 5758, American Association for the Advancement of Science, Washington, DC; US—ISSN 0036-8075.
"*Medicago truncatula* chromosome 7 clone mth2-71o19, complete sequence", EMBL, Jul. 21, 2004.
Jaskiewicz et al., "Role of Dicer in posttranscriptional RNA silencing", Current Topics in Microbiology and Immunology, Jan. 1, 2008, pp. 77-97, vol. 320, Springer, Berlin, DE—ISSN 0070-217X.
Qingpo et al., "Dicer-like (DCL) proteins in plants", Functional & Integrative Genomics, Feb. 17, 2009, pp. 277-286, vol. 9, Nr: 3, Springer, Berlin, DE—ISSN 1438-7948.
"Q2HTA7 (Q2HTA7_MEDTR) Unreviewed, UniProtKB/TrEMBL", Mar. 21, 2006.
Capitão et al., "In *Medicago truncatula*, water deficit modulates the transcript accumulation of components of small RNA pathways", BMC Plant Biology, 2011, 11:79, http://www.biomedcentral.com/1471-2229/11/79.
Olmedo, "Processing precursors with RNase III in plants", Plant Science, 2008, 175(6): pp. 741-746.
Sambrook, et al., "Small-Scale Preparations of Plasmid DNA", Molecular Cloning a Laboratory Manual, 1989, pp. 1.25-1.28, Cold Spring Harbor Laboratory Press.
Margis, et al., "The evolution and diversification of Dicers in plants", FEBS Letters 580, 2006, pp. 2442-2450, Elsevier B. V.
Finn, et al., "The Pfam protein families database", Nucleic Acids Research, 2010, vol. 38, Published online Nov. 17, 2009, Database issue D211-D222, Oxford University Press.

* cited by examiner

Primary Examiner — Suzanne M Noakes
(74) Attorney, Agent, or Firm — Walker & Jocke

(57) ABSTRACT

The subject of the invention is a peptide with the enzymatic activity of a Dicer-like protein, a method for preparing short RNA molecules, and use thereof. The purpose of the solution was to develop a new method of producing short RNA molecules, using a new, MtDCL1pepA peptide of a Dicer protein activity designed by inventors.

4 Claims, 4 Drawing Sheets

SEQUENCE LISTING

```
<160> NUMBER OF SEQ ID NOS: 6

<210> SEQ ID NO 1
<211> LENGTH: 733
<212> TYPE: PRT
<213> ORGANISM: Medicago truncatula
<220> FEATURE:
```

```
<221> NAME/KEY: SOURCE
<222> LOCATION: 1..733
<223> OTHER INFORMATION: /mol_type="protein"
      /organism="Medicago truncatula"

<400> SEQUENCE: 1
```

Asp Val Val Lys Ala Ser Gly Leu Val Pro Asn Arg Asp Ser Met Glu
1               5                   10                  15

Thr Gln Asn His Ile Asn Met Thr Thr Lys Gly Lys Leu Met Met Ala
            20                  25                  30

Asp Thr Cys Thr Ser Pro Asp Asp Leu Val Gly Arg Ile Val Thr Ala
            35                  40                  45

Ala His Ser Gly Lys Arg Phe Tyr Val Asp Ser Ile Arg Tyr Glu Met
    50                  55                  60

Thr Ala Glu Asn Ser Phe Pro Arg Lys Glu Gly Tyr Leu Gly Pro Leu
65                  70                  75                  80

Glu Tyr Ser Ser Tyr Ala Asp Tyr Tyr Lys Gln Lys Tyr Gly Val Asp
                85                  90                  95

Leu Ala Tyr Lys Gln Gln Pro Leu Ile Arg Gly Arg Gly Val Pro Tyr
            100                 105                 110

Cys Lys Asn Leu Leu Ser Pro Arg Phe Glu His Ser Gly Gly His Glu
            115                 120                 125

Asp Glu Thr Glu Glu Thr His Asp Lys Thr Tyr Tyr Val Phe Leu Pro
130                 135                 140

Pro Glu Leu Cys Leu Val Pro Pro Leu Pro Gly Ser Leu Val Arg Gly
145                 150                 155                 160

Ala Gln Arg Leu Pro Ser Ile Met Arg Arg Val Glu Ser Met Leu Leu
                165                 170                 175

Ala Val Gln Leu Lys Asn Met Ile Asn Tyr Pro Val Gln Ala Ser Lys
            180                 185                 190

Ile Leu Glu Ala Leu Thr Ala Ala Ser Cys Gln Glu Thr Phe Cys Tyr
            195                 200                 205

Glu Arg Ala Glu Leu Leu Gly Asp Ala Tyr Leu Lys Trp Val Val Ser
210                 215                 220

Arg Phe Leu Phe Leu Lys His Pro Gln Lys His Glu Gly Gln Leu Thr
225                 230                 235                 240

Arg Met Arg Gln Gln Met Val Ser Asn Met Val Leu Tyr Arg Tyr Ala
                245                 250                 255

Leu Ser Lys Gly Leu Gln Ser Tyr Ile Leu Ala Asp Arg Phe Ala Pro
            260                 265                 270

Ser Arg Trp Ala Ala Pro Gly Val Leu Pro Val Phe Asp Glu Asp Thr
            275                 280                 285

Lys Asp Glu Glu Ser Ser Leu Phe Asp Gln Arg Ser Ile Phe Lys
290                 295                 300

Ala Glu Arg Met Asp Asn Thr Asp Glu Phe Glu Asp Glu Met Glu Asp
305                 310                 315                 320

Gly Glu Leu Glu Ser Asp Ser Ser Tyr Arg Val Leu Ser Ser Lys
                325                 330                 335

Thr Leu Ala Asp Val Val Glu Ala Leu Ile Gly Val Tyr Tyr Val Glu
            340                 345                 350

Gly Gly Lys Asn Ala Ala Asn His Leu Met Lys Trp Ile Gly Ile His
            355                 360                 365

Ile Glu Ile Asp Pro Asp Glu Met Glu Cys Ile Thr Arg Pro Ser Asn
370                 375                 380

Val Pro Asp Ser Ile Leu Arg Ser Val Asp Phe Asp Ala Leu Glu Gly
385                 390                 395                 400

Ala Leu Asn Ile Lys Phe Lys Asp Lys Gly Leu Leu Ile Glu Ser Ile
            405                 410                 415

Thr His Ala Ser Arg Pro Ser Ser Gly Val Ser Cys Tyr Gln Arg Leu
        420                 425                 430

Glu Phe Val Gly Asp Ala Val Leu Asp His Leu Ile Thr Arg His Leu
    435                 440                 445

Phe Phe Ser Tyr Thr Asp Leu Pro Pro Gly Arg Leu Thr Asp Leu Arg
    450                 455                 460

Ala Ala Ala Val Asn Asn Glu Asn Phe Ala Arg Val Thr Val Lys His
465                 470                 475                 480

Asn Leu His Leu His Leu Arg His Gly Ser Ser Ala Leu Glu Lys Gln
            485                 490                 495

Ile Lys Asp Phe Val Arg Glu Val Gln Asp Glu Leu Ser Lys Pro Gly
        500                 505                 510

Phe Asn Ser Phe Gly Leu Gly Asp Cys Lys Ala Pro Lys Val Leu Gly
    515                 520                 525

Asp Ile Leu Glu Ser Ile Ala Gly Ala Ile Phe Leu Asp Ser Gly Arg
    530                 535                 540

Asn Thr Ala Val Val Trp Lys Val Phe Gln Pro Leu Leu His Pro Met
545                 550                 555                 560

Val Thr Pro Glu Thr Leu Pro Met His Pro Val Arg Glu Leu Gln Glu
            565                 570                 575

Arg Cys Gln Gln Gln Ala Glu Gly Leu Glu Tyr Arg Ala Ser Arg Ala
        580                 585                 590

Gly Asn Leu Ala Thr Val Glu Val Phe Ile Asp Gly Val Gln Val Gly
    595                 600                 605

Ala Ala Gln Asn Pro Gln Lys Lys Met Ala Gln Lys Leu Ala Ala Arg
    610                 615                 620

Asn Ala Leu Ala Ala Leu Lys Glu Lys Glu Glu Ser Lys Ile Gln Glu
625                 630                 635                 640

Lys Asn Asp Glu Lys Glu Thr Lys Ser Gly Asn Gln Thr Phe Thr Arg
            645                 650                 655

Gln Thr Leu Asn Asp Ile Cys Leu Arg Arg Asn Trp Pro Met Pro Phe
        660                 665                 670

Tyr Arg Cys Val Ser Glu Gly Gly Pro Ala His Ala Lys Lys Phe Thr
    675                 680                 685

Phe Ala Val Arg Val Asn Thr Thr Asp Lys Gly Trp Thr Asp Glu Cys
    690                 695                 700

Val Gly Glu Pro Met Pro Ser Val Lys Lys Ala Lys Asp Ser Ala Ala
705                 710                 715                 720

Val Leu Leu Leu Glu Leu Ile Asn Lys Leu Tyr Ser Ser
            725                 730

<210> SEQ ID NO 2
<211> LENGTH: 29
<212> TYPE: DNA
<213> ORGANISM: Medicago truncatula
<220> FEATURE:
<221> NAME/KEY: source
<222> LOCATION: 1..29
<223> OTHER INFORMATION: /mol_type="DNA"
      /organism="Medicago truncatula"

<400> SEQUENCE: 2

-continued

```
tagaataggc gttgatacac agcaatagg                                      29

<210> SEQ ID NO 3
<211> LENGTH: 25
<212> TYPE: DNA
<213> ORGANISM: Medicago truncatula
<220> FEATURE:
<221> NAME/KEY: source
<222> LOCATION: 1..25
<223> OTHER INFORMATION: /mol_type="DNA"
      /organism="Medicago truncatula"

<400> SEQUENCE: 3
acaaccactg cttgcttctg attgg                                          25

<210> SEQ ID NO 4
<211> LENGTH: 33
<212> TYPE: DNA
<213> ORGANISM: Medicago truncatula
<220> FEATURE:
<221> NAME/KEY: source
<222> LOCATION: 1..33
<223> OTHER INFORMATION: /mol_type="DNA"
      /organism="Medicago truncatula"

<400> SEQUENCE: 4
ccgaattccg atgtagtgaa agcttcagga ttg                                 33

<210> SEQ ID NO 5
<211> LENGTH: 58
<212> TYPE: DNA
<213> ORGANISM: Medicago truncatula
<220> FEATURE:
<221> NAME/KEY: source
<222> LOCATION: 1..58
<223> OTHER INFORMATION: /mol_type="DNA"
      /organism="Medicago truncatula"

<400> SEQUENCE: 5
gtgagccttg tcatcgtcgt ccttgtagtc tgacgagtat aatttgttta ttagttcc      58

<210> SEQ ID NO 6
<211> LENGTH: 50
<212> TYPE: DNA
<213> ORGANISM: Medicago truncatula
<220> FEATURE:
<221> NAME/KEY: source
<222> LOCATION: 1..50
<223> OTHER INFORMATION: /mol_type="DNA"
      /organism="Medicago truncatula"

<400> SEQUENCE: 6
gtagtcgact cagtgtttgt gacggtggtt gtgagccttg tcatcgtcgt               50
```

PEPTIDE WITH THE ENZYMATIC ACTIVITY OF A DICER-LIKE PROTEIN, A METHOD FOR PREPARING SHORT RNA MOLECULES, AND USE THEREOF

The subject of the invention is a peptide with the enzymatic activity of a Dicer-like protein, a method for preparing short RNA molecules and use thereof.

Eukaryotic organisms (plants and animals including a human) have the ability to generate short RNA molecules of about 20-25 nucleotides in length involved in the regulation of gene expression. Regulation of gene expression by short RNA molecules is present in many important physiological processes (proliferation and cell differentiation, programmed cell death) as well as in pathological ones (carcinogenesis, viral infections, neurodegenerative processes). A specific enzyme is required for the formation of short RNA molecules—a protein showing similarity to RNase III. Such protein, depending on the origin may bear different names, in the case of a human it is called Dicer, in the case of plants—a Dicer-like protein (DCL).

Most of Dicer-like proteins (Dicer and DCL) that occur in vertebrates, insects and plants have six types of domains in their structure: DEAD cassette, C helicase, DUF283 (domain of unknown function), PAZ (Piwi/Argonaute/Zwill), RNase III and RBD (dsRNA binding domain) [Margis et al.]. In lower eukaryotes, proteins from Dicer family are deprived of one or more of these domains. For example, Dicer protein from the *Giardia intestinalis* protozoan contains only the PAZ and the RNase III domain [Macrae et al.]. This indicates the crucial role of these two domains in the catalytic activity of a Dicer-like protein.

Dicer-like protein action is to cut out short 20-25 nucleotide RNA duplex from a larger precursor molecule. For Dicer-like protein to properly fulfil its role it must be able to recognize a double-stranded region, from which short dsRNA is to be cut out and to cut very precisely, so that the obtained molecule meets strictly defined parameters. Not only the length of the RNA duplex is important, but also its structure. It must have two unpaired, free nucleotides at the 3' end. It should be noted that the dsRNA molecules that do not meet these criteria will not be effectively incorporated into the RISC (RNA-induced silencing complex), which participates in the regulation of gene expression. After incorporating a short duplex into the RISC, one of the RNA strands is removed and degraded, while the other serves as a specific probe capable of recognizing a complementary RNA or DNA molecule (of a gene).

In recent years, short RNA molecules are becoming more widely used both in biotechnology and in medicine. Techniques utilizing short RNA molecules to regulate gene expression are used for both cognitive (e.g., to study gene function) and practical purposes (to obtain favourable features in plants and animals in terms of their utility). In addition, new therapeutic methods are developed based on preparations containing short RNA molecules. Most of these techniques require the use of Dicer or DCL protein in order to receive short dsRNAs. Currently, the commercial kits used in the study of a biological activity of short regulatory RNAs include, but are not limited to, the protein extract enriched in human Dicer or from *Giardia intestinalis*.

With regard to existing patents on phenomena related to RNAi, most of them concern the human DICER protein—substantially different from the present invention at the level of the amino acid sequence, and the application of artificial transgenes—containing short sequences coding molecules of specific RNAi, directed to specific genes—for plant transformation and modulation of their phenotype.

In the patent application WO 2009/117513 (published on 2009 Sep. 24) a modified Dicer polypeptide, which exhibits enhanced catalytic activity was described. The solution provides also a method for the preparation of small regulatory RNAs from dsRNA, including contact of dsRNA with the present modified Dicer.

In the patent application US 20100058490 (published on 2010 Mar. 4) methods for gene silencing were described. The solution presents also the methods and means of modulating gene silencing in eukaryotes through a change in the level of functional DICER protein and DICER-like proteins. The solution presents also methods and means of modulating post-transcriptional gene silencing in eukaryotes through a change in the functional level of proteins involved in transcriptional silencing of a gene encoding the silenced RNA.

In spite of existing solutions using short RNA molecules to regulate the gene expression used both for studying gene function and obtaining, but not limiting to features favourable in terms of utility in plants and animals, there is a continuous need for the production of short RNA molecules of a Dicer protein activity.

The aim of a present solution was to develop a new method of producing short RNA molecules, using a new, MtDCL1pepA peptide of a Dicer protein activity designed by the inventors.

Fulfillment of such specified purpose and solving the problems described in the prior art associated with the development and delivery of a peptide of a Dicer activity, distinguishing it from occurring in the available preparations in terms of origin and optimized physiochemical and biochemical parameters, soluble in aqueous solutions, have been achieved in the present invention.

The above characteristics of the MtDCL1pepA peptide translate into a number of advantages of the proposed method of obtaining short regulatory RNAs. The proposed method can be considerably cheaper than other currently used as MtDCL1pepA protein can be produced both in the eukaryotic system, and, what is the unique feature of the MtDCL1pepA peptide, in a cheap and highly efficient prokaryotic system. This system also allows to obtain a preparation of extremely high purity, far exceeding the other so far described preparations. The proposed method, due to the use of plant enzyme, enables detailed studies of RNA interference phenomenon in plants—so far there is no possibility of producing short regulatory RNA using a commercial plant-based enzyme.

The subject of the invention is a peptide, characterized in that it comprises a MtDCL1pepA peptide determined by SEQ ID NO: 1 sequence with the enzymatic activity of a Dicer-like protein.

Advantageously, when peptide contains a MtDCL1pepA peptide its significant fragment comprising at least a half of MtDCL1pepA sequence or sequences at the level of amino acid sequence similarity of at least 80%.

Advantageously, when peptide contains a MtDCL1pepA peptide containing only the selected domains necessary to preserve their own catalytic activity, and not having 1154 amino acids from the N-terminus of MtDCL1 protein, and that the MtDCL1pepA peptide contains PAZ domain, two RNase III domains and two RBD domains.

Advantageously, when the MtDCL1pepA peptide is provided with tags.

Advantageously, when the tags include glutathione S-transferase peptide (GST) at the N-terminus of MtDCL1pepA and two FLAG and hexahistidine (His) tags at the C-terminus.

Advantageously, when a MtDCL1pepA peptide is produced in a prokaryotic or eukaryotic system.

Another example of the invention is a method for preparing short RNA molecules, characterized in that the peptide defined above is used and that the method comprises:
- a) production of cDNA encoding the MtDCL1 peptide from the *Medicago truncatula* plant;
- b) reconstruction of the presumed sequence of cDNA (exons) of the gene encoding MtDCL1;
- c) design of DNA oligomers, J08-10 defined by the SEQ ID NO:2 and J08-13 defined by SEQ ID NO: 3, enveloping the sequence encoding the MtDCL1 protein;
- d) carrying out the synthesis of first cDNA strand using RNA originate from young leaves and young top parts of above-ground shoots of *Medicago truncatula*;
- e) second cDNA strand synthesis and cDNA amplification;
- f) cloning of cDNA encoding MtDCL1, but the cDNA is introduced into a plasmid vector, the transformation of bacteria is carried out and a culture of those with an insert of 5500 by in length is cultivated;
- g) isolation of plasmid DNA for sequencing;
- h) obtaining MtDCL1 protein sequence and subjecting it to bioinformatic analysis for the content of the known functional domains, characteristic for most Dicer-like proteins: DEAD cassette, helicase C, DUF283, PAZ, RNase III and RBD;
- i) designing truncated MtDCL1pepA protein containing only the selected domains necessary to preserve their own catalytic activity, and not having 1154 amino acids from the N-terminus of MtDCL1 protein, but the deleted fragment includes the DEAD cassette, helicase C domain and DUF283, and the MtDCL1pepA peptide contains PAZ domain, two RNase III domains and two RBD domains.

Advantageously, when the MtDCL1pepA peptide is being provided with tags.

Advantageously, when the tags include glutathione S-transferase peptide (GST) at the N-terminus of MtDCL1pepA and two FLAG and hexahistidine (His) tags at the C-terminus.

Another subject of the invention is the use of a peptide defined above to generate a short 15-30 nucleotide RNA molecules.

The structure of sequence of clone 44-57 reveals that this clone contains the complete sequence encoding the DCL1 peptide—upstream the start of translation, position 79, are 78 nucleotides and downstream the stop codon, position 5742, is 42 nucleotide non-coding segment. The coding region (CDS) of clone 44-57—lying between positions 79 and 5742—contains all domains characteristic for DCL peptides. Lower similarity between the cDNA-sequence of clone 44-57 and genomic sequence derived from clone mth2-71o19 (accession number AC150443) is visible within exons 13 and 15. The analysis was made using the Blastn program.

Figure 3:
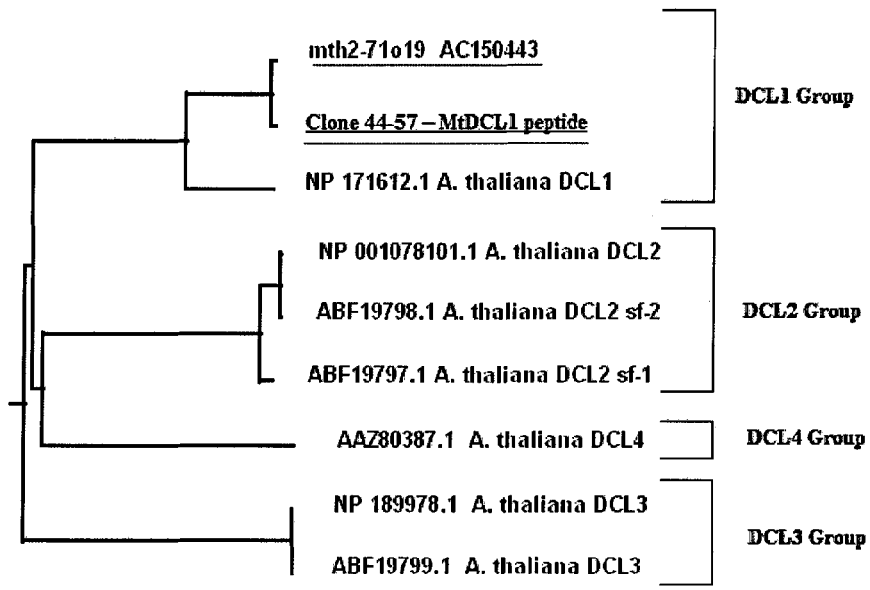

FIG. 3 shows the phylogenetic tree of DCL peptides from *M. truncatula* and *A. thaliana*. The tree was obtained by NJ method (Neighbourhood-Joining) based on the ordered sequences in ClustalW program. Genes for the four types of DCL proteins, called: DCL1, DCL2, DCL3 and DCL4 are present in the model *A. thaliana* plant. Some of these proteins are present in several splicing forms—marked in the figure as "-sf". Four types of DCL proteins present in *A. thaliana* have a similar molecular mechanism of action but differ in function. It is believed that in other plants genes for all four types of DCL proteins, such as *A. thaliana* are also present, but sometimes there may have been a duplication of some genes, which led to origin of closely-related groups called gene families. Phylogenetic analysis of the studied peptide derived from *M. truncatula*—a peptide encoded by the clone 44-57—against all DCL peptides from *A. thaliana* assigns the studied peptide to the orthologous peptide. The presented phylogenetic tree shows that the relationship between the MtDCL1 peptide encoded by clone 44-57 and the DCL1 peptide from *A. thaliana* is greater than between the DCL1 peptide from *A. thaliana* and any other DCL peptide from *A. thaliana*. Thus is sought that MtDCL1 peptides from *M. truncatula* and DCL1 from *A. thaliana* are an orthologous peptides. The analysis includes a peptide obtained as a result of bioinformatic sequence analysis of genomic clone from *M. truncatula* mt2-71o19 (accession number AC150443). Phylogenetic analysis was performed with a set of programs available on the website http://align.genome.jp. In the case of peptides from *A. thaliana* names are given as DCL1, DCL2 and accession numbers of peptides, for the peptide derived from genomic clone MT2-71o19 (highlighted by a single underline) nucleotide sequence accession number are given, the peptide encoded by cDNA sequence of clone 44-57 obtained by the authors is marked as MtDCL1 peptide (highlighted by double underline).

Figure 4:
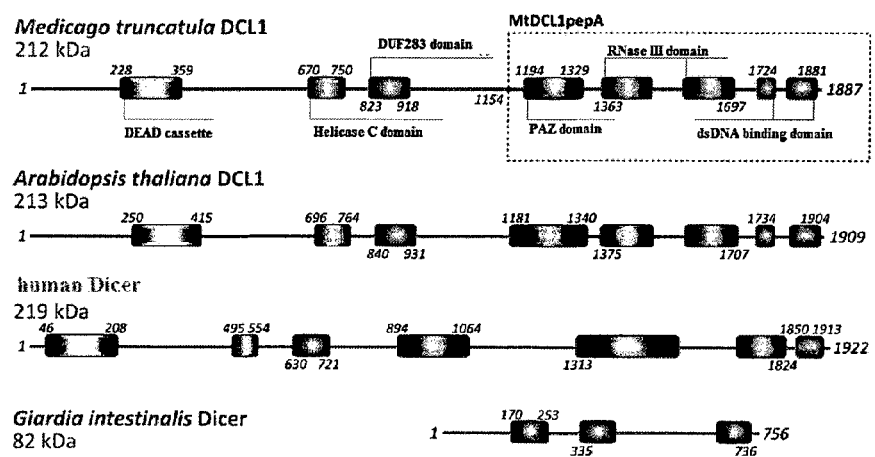
Figure 5:
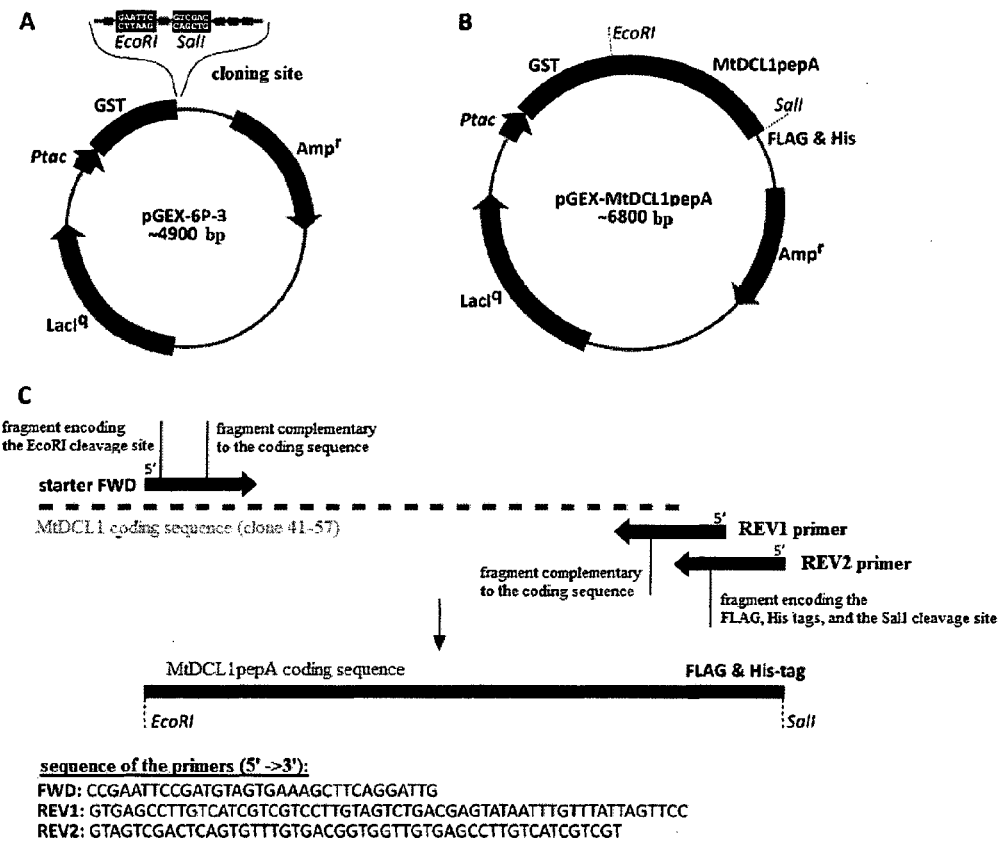

FIG. 4 shows the domain structure of a Dicer-like protein from *Medicago truncatula* and *Arabidopsis thaliana*, human and protozoan *Giardia intestinalis*. The active fragment of DCL1 protein from *M. truncatula*—MtDCL1pepA was also marked. Domain identification was made by the EIB EMBL InterProScan [x3] tool;

FIG. 5 shows: (A) the scheme of the structure of pGEX6P3 expression vector (GE Healthcare), (B) the scheme of the pGEXMtDCL1pepA expression vector, obtained from the pGEX6P3 vector and a coding sequence of MtDCL1pepA, used in the production of a MtDCL1pepA peptide in bacterial cells. The schemes show, but are not limited to the location of MtDCL1pepA protein coding sequences, GST, FLAG, and His tags, location of tac promoter (Ptac), selective gene and restriction sites used in the cloning procedure of MtDCL1pepA sequence;

(C) the PCR reaction scheme used for amplification of the DNA encoding the MtDCL1pepA protein. The structure of primers has been indicated as FWD (SEQ ID NO: 4), REV1 (SEQ ID NO: 5), and REV2 (SEQ ID NO: 6).

Figure 6:
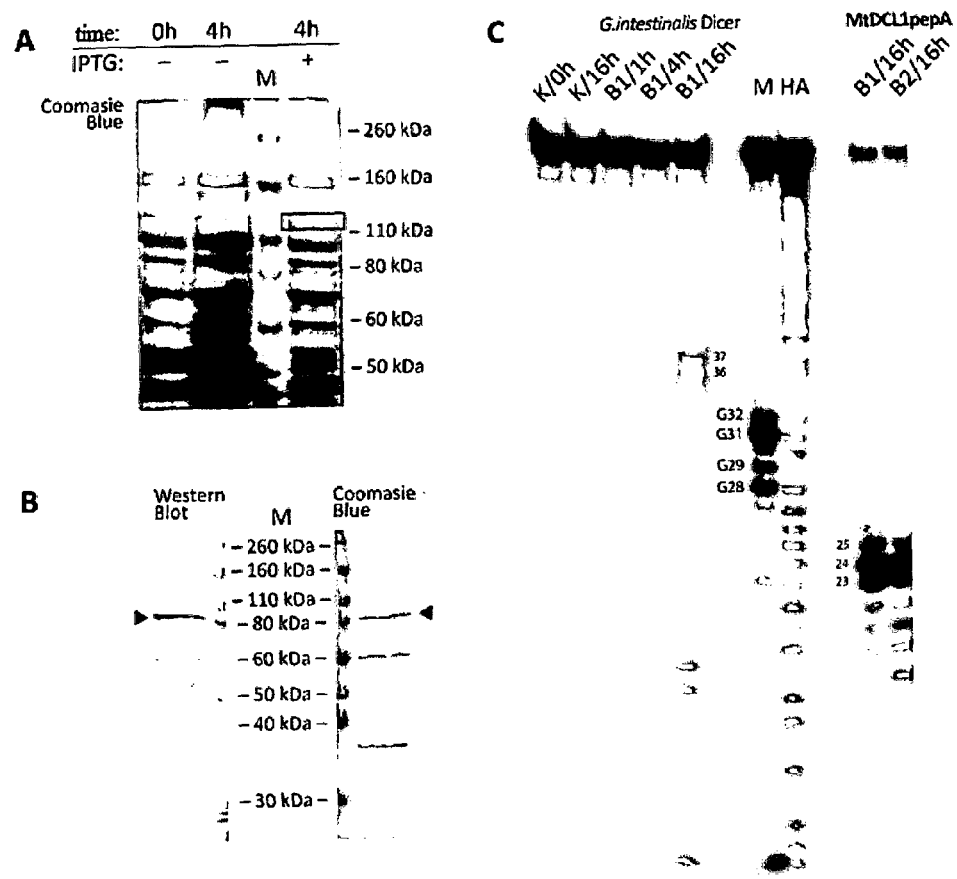

FIG. 6 shows: (A) the result of the expression of a plasmid encoding the MtDCL1pepA protein provided with a GST tag at the N-terminus and FLAG and His at the C-terminus (the mass of the entire fusion protein was 112 kDa). Separation of protein fractions isolated from the bacterial culture samples of strain transformed with an expression vector was made on the 10% PAA gel with SDS. Samples were taken immediately before induction of expression (time 0 h) and 4 hours after the addition of an inducer—IPTG. At the same time a control culture was carried out without the addition of an inducer of expression. The gel was stained with a Comassie Blue dye; (B) the obtained protein preparation enriched in a DCL1pepA protein free of GST tag at the N-terminus (weight of a protein: 86 kDa). The preparation was separated on 10% PAA gel with SDS. The purity of a preparation is illustrated by the gel stained with Comassie Blue dye, the protein was identified by Western Blot technique; (C) comparison of DCL1pepA protein activity and commercially available Dicer protein from *Giardia intestinalis*. The DCL1pepA protein generates products of approximately 20-25 bp in the reaction with the precursor of human miRNA 33a (66 bp) in the presence of two different buffering solutions (B1, B2). Comparison of a recombinant Dicer protein from *Giardia intestinalis* generates, in the presence of an identical substrate, products with a greater range of length, with a predominance of 36-37 nucleotide fragments. Reactions were carried out in an optimized buffering solution attached to the Dicer protein from *Giardia intestinalis* (B1 mark) or 20 mM Tris-HCl pH 7.5 buffer with 250 mm NaCl, 2.5 mM $MgCl_2$ (B2 mark). M—molecular weight marker, K—control (reaction mixture without the addition of an enzyme), HA—miRNA 33a substrate subjected to an alkaline hydrolysis, h—reaction time in hours.

DETAILED DESCRIPTION

The embodiments according to the invention are shown below for better understanding of the invention.

Example

There is no deposited cDNA sequence for the DCL1 protein from *M. truncatula* (MtDCL1) in the sequence databases (GenBank). There is only available a gene sequence (composed of introns and exons) and an artificial sequence of cDNA obtained as a result of bioinformatic gene sequence processing. The known cDNA sequence of MtDCL1 differs slightly from the artificial MtDCL1 cDNA sequences obtained as a result of a bioinformatic genomic sequence processing.

cDNA encoding a DCL1 peptide from the *Medicago truncatula* plant (hereinafter referred to as MtDCL1) was obtained using RT PCR technique and cloning using homology. In the first stage the database of *Medicago truncatula* sequences in GenBank was researched with the use of amino acid sequence of a DCL1 protein from *Arabidopsis thalian*, accession number NP_171612.1 and tblastn program. The sequence region of a mth2-71o19 clone [119169-109079] from *Medicago truncatula* with accession number AC150443 was selected for further work, for which the similarity with the DCL1 protein sequence from *Arabidopsis thalian* (accession no. NP_171612.1) is characterized by the lowest expected value.

Region [119169-109079] of the mth2-71o19 clone sequence from *Medicago truncatula* with accession number AC150443 was used to reconstruct the presumed cDNA sequence containing the complete coding sequence of MtDCL1 protein. Reconstruction of the presumed cDNA sequence (exons) of gene encoding MtDCL1 was performed by comparing the sequence region of a mth2-71o19 clone [119169-109079] (accession number AC150443) with the coding sequence of DCL1 from *Arabidopsis thaliana* with the accession number NM_099986 using Spidey program (www.ncbi.nlm.nih.gov/spidey), and by comparing the amino acid sequence obtained by translating the sequence of mth2-71o19 clone (accession number AC150443) with the DCL1 protein sequence from *Arabidopsis thaliana*. Bioinformatic sequence translation of mth2-71o19 clone (accession number AC150443) was made using programs from the Sequence Manipulation Suite (http://www.bioinformatics.org/sms2). It is assumed that the sequence region of a mth2-71o19 clone [119169-109079], accession number AC150443 contains the complete sequence encoding the DCL1 protein from *M. truncatula* and part or all of the cDNA untranslated regions (UTR). Then two DNA oligomers—J08-10 and J08-13 were designed, enveloping the sequence encoding the MtDCL1 protein, whose sequence was in 100% identical to the selected portions of the sequence region of a mth2-71o19 clone [119169-109079] (accession number AC150443). DNA oligomer named J08-10 consisted of 29 nucleotides and had the SEQ ID NO: 2: TAGAATAGGCGTTGATACACAGCAATAGG, while the J08-13 oligomer having the SEQ ID NO: 3: ACAACCACTGCTTGCTTCTGATTGG consisted of 25 nucleotides (sequences given in accordance with the convention from the 5' to 3' end).

Figure 1:
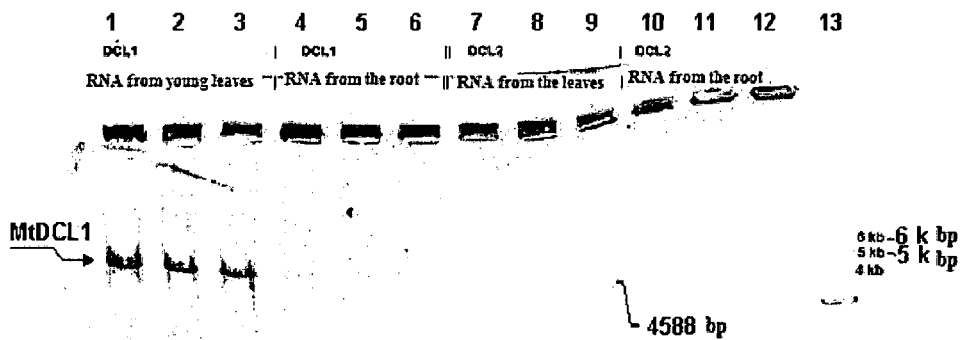
FIG. 1 shows amplification of cDNA encoding a MtDCL1 peptide. Lines 1, 2, 3-PCR product obtained as a result of cDNA amplification from young leaves and top parts of an above-ground shoot of *M. truncatula* using the DNA oligomers: J08-10 and J08-13. The size of the product matches the expected one for DCL1 cDNA from *M. truncatula*—5784 base pairs, estimated on the basis of bioinformatic analysis of cDNA for DCL1 from other organisms and genomic clone sequence from *M. truncatula*—mth2-71o19, accession number AC150443.
Figure 2:
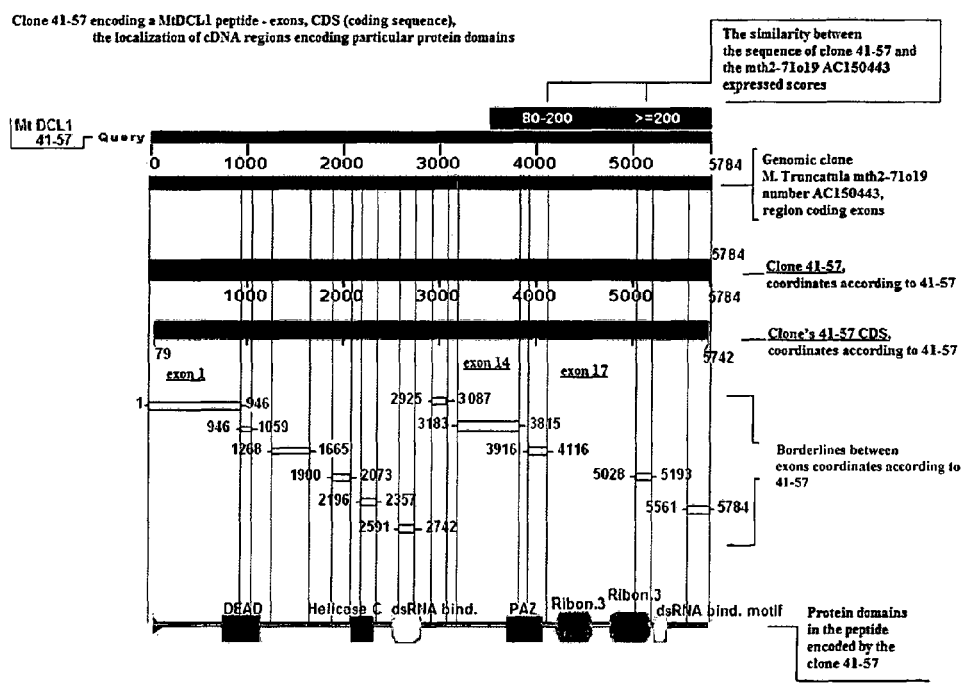
FIG. 2 shows the structure of a clone 44-57 encoding the DCL1 peptide of *M. truncatula*. Comparison of cDNA sequence—clone 44-57 with the sequence of genomic clone mth2-71o19 (accession number AC150443) reveals the borderlines between exons marked as vertical black lines; exon 1, 14 and 17 have been signed, and exons 1, 2, 4, 6, 8, 10, 12, 14, 16, 18 and 20 are marked as rectangles, the borderlines between exons were determined according to coordinates referring to the sequence of clone 44-57. Encoding part of a clone 44-57, marked as the CDS (coding sequence) and marked in green, is located between position 79 and 5742 of clone 44-57. The location of the regions encoding a specific protein domains in MtDCL1 44-57 pep—tide encoded by the clone 44-57 and their localization in relation to the boundaries between exons were also shown.

In the next stage of the works the first cDNA strand synthesis reaction was carried out using 2 micrograms of RNA from young leaves and young, top parts of above-ground shoots of *Medicago truncatula* R108 per 20 microliters of the reaction mixture and the DNA oligomer (dT)18 at a final concentration of 2.5 micromol/L, DTT at a final concentration of 10 mmol/L, dATP at a final concentration of 0.5 mmol/L, dCTP at a final concentration of 0.5 mmol/L, dGTP at a final concentration of 0.5 mmol/L, dTTP at a final concentration of 0.5 mmol/L, an RNase inhibitor—RNaseOUT (Invitrogen) at a final concentration of 2 units/microliter, and a buffer for reverse transcription from the SuperScript II Reverse Transcriptase kit (Invitrogen) and an enzyme—SuperScript II Reverse Transcriptase (Invitrogen) at a concentration of 10 units/microliter. The reaction of first cDNA strand synthesis was performed according to the SuperScript II Reverse Transcriptase kit (Invitrogen) supplier's recommendations, with the fact that incubation was carried out at 42° C. for 55 minutes. Single-stranded cDNA obtained by this reaction was then used, without purifying it from other components of the reverse transcription reaction, in the second cDNA strand synthesis and the cDNA amplification in a PCR reaction using a FastStart High Fidelity PCR System pack from Roche. The PCR reaction was performed in a buffer 2 (containing magnesium chloride at a final concentration in the reaction mixture of 1.8 mmol/L) from the FastStart High Fidelity PCR System pack (Roche) using 1 microliter of reverse transcription reaction (described above) at a final volume of the reaction mixture of 50 microliters. The reaction mixture consisted of: DMSO at a final concentration of 2%, dATP at a concentration of 0.2 mmol/L, dCTP at a concentration of 0.2 mmol/L, dGTP at a concentration of 0 2 mmol/L, dTTP at a concentration of 0.2 mmol/L, J08-10 DNA oligomer (sequence see above) at a concentration of 0.3 micromoles/L, J08-13 DNA oligomer (sequence see above)

at a concentration of 0.3 micromoles/L, and a mixture of enzymes from the FastSart High Fidelity PCR System pack (Roche) at a concentration final 0.05 unit/microliter. The PCR reaction was performed using the following program: first stage—incubation at 94° C. for 2 minutes, second stage: ten times the sequence of incubation: incubation at 94° C. for 30 s, incubation at 53° C. for 30 s, incubation at 68° C. for 6 minutes, third stage: twenty-five times the sequence of incubation: incubation at 94° C. for 30 s, incubation at 55° C. for 30 s, incubation at 68° C. for 6 minutes with prolonged incubation time of 10 seconds at each successive cycle, fourth stage: one time incubation at 68° C. for 7 minutes ended with cooling the reaction to 4° C. As a result a product of approximately 5784 bp (base pairs) was obtained, FIG. 1. PCR reaction product was purified on 0.7% agarose gel, from which the DNA with a length of fragments of approximately 5784 bp was cut out and the DNA extraction was performed from the agarose gel with the QIAquick Gel Extraction Kit from Qiagen following the kit manufacturer's instruction. DNA preparation was obtained with a length of molecules of approximately 5784 bp and a concentration of about 15 ng/microliter, which was used for the next stage—the cloning of cDNA encoding the MtDCL1. First the introduction of the studied DNA into a pCR-XL-TOPO plasmid vector (Invitrogen) was performed. The reaction was carried out according to the instructions provided by the TOPO XL PCR Cloning Kit manufacturer—the Invitrogen company, using 0.5 microliters of the above-described preparation containing the cloned cDNA encoding the MtDCL1 and 2.5 microliters of the mixture containing the activated plasmid and an enzyme from a TOPO XL PCR Cloning Kit (Invitrogen). After the end of the reaction, in which the cDNA is incorporated into a plasmid vector giving the recombinant plasmids, the One Shot TOP 10 Electrocomp E. coli (Invitrogen) bacteria transformation was carried out according to manufacturer's instruction. 40 microliters of bacteria, 1 microliter of recombinant plasmid, electroporation cuvettes with electrodes distance of −1 mm and Gen-Pulser electroporator from Biolabs company were used in the transformation. 1250 V, 25 microfarads and 200 Ohms were used in order to administer an electric pulse. After the incubation of transformation mixture with 250 microliters of SOC medium at 37° C. for 75 min., 20 microliters and 200 microliters of bacteria were seeded on the petri dish containing solid LB medium with kanamycin at a concentration of 50 micrograms/ml as a selective agent and they were incubated in 37° C. for 20 hours. 19 colonies were received and studied, three of which had an insert of the expected length—approximately 5784 bp. Breeding of these clones was carried out in 20 ml of liquid medium and isolated—with the use of alkaline lysis method [Sambrook et al.]—Plasmid DNA, which was used for sequencing. Sequence analysis showed that only one clone named 41-57 contains the complete coding sequence of DCL1 peptide derived from *Medicago truncatula* (MtDCL1), FIG. 2. Confirmation that the peptide encoded by clone 44-57 is equivalent to *M. truncatula* DCL1 peptide from *A. thaliana* was obtained as a result of phylogenetic analysis—FIG. 3, and table Tab. 1.

Table 1. Comparison of DCL1 peptides from *Medicago truncatula*—i.e. MtDCL1 peptide encoded by a clone 44-57 and a peptide obtained from the bioinformatic analysis of 9 genomic clone mth2-71o1, accession number AC150443 with peptides DCL1, DCL2, DCL3 and DCL4 from *Arabidopsis thaliana*.

TABLE 1

| The similarity between the DCL peptides from *M. truncatula* and *A. thaliana*. [%] | | | | | | |
|---|---|---|---|---|---|---|
| | MtDCL1 clone 44-57 | mth2-71o19 AC150443 | AthDCL1 NP171612.1 | AthDCL2 NP001078101 | AthDCL3 ABF19799.1 | AthDCL4 AAZ80387.1 |
| MtDCL1 Clone 44-57 | 100% | 99.57% | 86.54% | 45.73% | 43.13% | 41.39% |
| mth2-71o19 AC150443 | 99.57% | 100% | 86.98% | 45.88% | 43.27% | 41.53% |
| AthDCL1 NP171612.1 | 86.54% | 86.98% | 100% | 45.88% | 43.70% | 40.96% |
| AthDCL2 NP001078101 | 45.73% | 45.88% | 45.88% | 100% | 40.81% | 40.81% |
| AthDCL3 ABF19799.1 | 43.13% | 43.27% | 43.70% | 40.81% | 100% | 38.49% |
| AthDCL4 AAZ80387.1 | 41.39% | 41.53% | 40.96% | 40.81% | 38.49% | 100% |

The degree of similarity between a pair of peptides is expressed as a percentage of identical amino acids at corresponding positions of the compared peptides. The correlation of peptides assigning corresponding positions in a particular peptides was made with a ClustalW program. Before analysing the degree of similarity peptides ordered by the ClustalW program have been subjected to a purification from the position of low correlation reliability and from regions that do not have counterparts in all the compared sequences using the Gblocks program. The analysis was performed using the software package available on websites http://www.phylogeny.fr and http://www.bioinformatics.org/sms2/.

Peptides derived from *M. truncatula*—MtDCL1 peptide encoded by clone 44-57 and the peptide obtained as a result of bioinformatic sequence analysis of genomic mth2-71o19 clone sequence (accession number AC150443) are almost two times more similar to a DCL1 peptide from *A. thaliana* than to the other DCL peptides from *A. thaliana*.

The similarity between the peptides derived from *M. truncatula*—MtDCL1 peptide encoded by the clone 44-57 and a peptide obtained as a result of bioinformatic sequence analysis of genomic mth2-71o19 clone sequence (accession number AC150443) is almost twice as high (1.89-2.10) as the similarity with other DCL peptides. This proves—similarly to the result of phylogenetic analysis, that a DCL1 peptide from *A. thaliana* is more closely related to MtDCL1 peptides and peptide obtained as a result of bioinformatic sequence analysis of genomic mth2-71o19 clone, than with other DCL peptides from *A. thaliana*.

Obtained MtDCL1 protein sequence (the result of the translation of DNA sequence of the gene present in clone 4157) was subjected to bioinformatic analysis for the contents of known functional domains, using the EMBLEBI InterProScan tool (http://www.ebi.ac.uk/Tools/ InterProScan). Six types of domains characteristic for most Dicer-like proteins were identified in the given sequence: DEAD cassette, helicase C, DUF283, PAZ, RNase III and RBD. FIG. 4 shows their detailed arrangement in MtDCL1 protein. Truncated protein was designed on the basis of this analysis, i.e. containing only the selected domains, necessary to maintain proper catalytic activity. Shortening of protein was a necessary manipulation in order to produce the protein in a cheap and efficient bacterial expression system. Dicer protein from protozoan *Giardia intestinalis*, which having only two types of domains: PAZ and RNase III, is catalytically active served as a model, when choosing domains. Designed truncated protein, hereinafter referred to as MtDCL1pepA, has no 1154 amino acids from the N-terminus of MtDCL1 protein. The deleted fragment includes the DEAD cassette, helicase C domain and DUF283. MtDCL1pepA peptide contains PAZ domain, two RNase III domains and two RBD domains, as shown in FIG. 4.

It was decided to supply MtDCL1pepA with few markers to raise the efficiency of expression and ensure that simple and effective methods of identification and purification of protein were used. And so a large glutathione S-transferase (GST) peptide was attached at the N-terminus of MtDCL1pepA, while two short tags: FLAG and hexahistidine (His) at the C-terminus. A pGEXMtDCLpepA expression vector, a derivative of commercially available pGEX6P3 plasmid (GE Healthcare) containing GST tag sequence (see FIG. 5) was prepared to receive the designed protein. AMtDCL1 gene fragment, encoding a selected fragment of protein (amino acids 1155-1887) with the FLAG and His tags was cloned into the pGEX6P3 plasmid.

DNA for cloning was obtained in two PCR reactions, using three different primers: primer FWD contained a cleavage site of an EcoRI enzyme and a fragment of a sequence complementary to the sequence encoding the N-terminus of a designed MtDCL1pepA protein, starter REV1 contained a fragment of a sequence complementary to the sequence encoding the C-terminus of MtDCL1pepA and a fragment of the sequence encoding the FLAG and His tags, while REV2 primer contained a fragment of a sequence encoding the FLAG and His tags, and a cleavage site of the SalI enzyme. The sequences of the REV1 and REV2 primers partially overlapped, to allow carrying out a PCR reaction using the REV2 on the matrix of PCR reaction product with REV1 primer (see FIG. 5). DNA of clone 41-57 and FWD and REV1 primers were used in the first PCR reaction, while in the second—FWD and REV2 primers and product of the previous PCR reaction purified using QIAquick PCR Purification Kit (QIAGEN). The composition of each PCR reaction (final concentrations, the volume of the reaction are given: 50 µl): DNA of clone 41-57 (100 ng/50 µl), FWD primer (1 µM), REV1 or REV2 primer (1 µM), dNTP mix (200 µM), reaction buffer from a Promega Pfu DNA Polymerase kit (1×), an enzyme from a Promega Pfu DNA Polymerase kit (1.25 U/50 µl), nuclease-free water. Reaction program: stage I (temp. 95° C.-2 min.), stage II (sequence: temp. 95° C.-1 min., 60° C.-30 sec., 72° C.-4 min.) repeated 30 times, stage III (temp. 72° C.-5 min.) The reaction product was purified using QIAquick PCR Purification Kit (QIAGEN) according to manufacturer's description. So prepared insert's DNA and DNA of pGEX6P3 vector were subjected to the reaction of digestion with EcoRI (Fermentas) and SalI (Fermentas) restriction enzymes. The composition of digestion reaction is given (final concentrations, the volume of the reaction: 40 µl): Insert's or vector's DNA (1 µg/40 µl), Fermentas buffer (1×), Fermentas EcoRI enzyme (5U/40 µl), Fermentas SalI enzyme (5U/40 µl), nuclease-free water. The reaction was carried out for 4 hours at 37° C. The product of each reaction was purified using QIAquick PCR Purification Kit (QIAGEN) according to manufacturer's description. Purified digestion products were subjected to the ligation reaction using a T4 DNA Ligase enzyme (Promega). The composition of a ligation reaction (final concentrations are given, the volume of the reaction: 20 µl): Vector's DNA (100 ng/20 µl), insert's DNA (200 ng/20 µl), buffer from Promega T4 DNA Ligase kit (1×), an enzyme from Promega T4 DNA Ligase kit (2U/20 µl), nuclease-free water. The reaction was carried out for 16 hours at 4° C. Competent *E. Coli* DH5α cells were transformed with the reaction product for selection and multiplication of properly constructed pGEXMtDCL1pepA plasmids. 5 µl of ligation product were added to 50 µl of competent cells suspension, the bacteria were mixed gently, incubated at 4° C. for 45 min. Then were subjected to thermal shock by incubating the suspension at 42° C. for 45 sec. and rapid cooling at 4° C. 1 ml of liquid LB medium was added to the suspension and shaken for one hour at 37° C. at a speed of 225 rpm. The suspension was spread onto two petri dishes with a solid LB medium with ampicillin. The petri dishes were incubated for 16 h at 37° C. 24 individual colonies of bacteria grown on solid LB medium with ampicillin were chosen, transferred to 2 ml of liquid LB medium containing ampicillin and shaken for 16 h at 37° C. at a speed of 300 rpm. Each culture was centrifuged at 14000 rpm for 1 min., the solution was decanted and plasmids from the precipitate containing the bacteria were isolated by alkaline lysis method. Each plasmid was purified using QIAquick PCR Purification Kit (QIAGEN) according to manufacturer's description and sequenced. In this way, a preparation containing properly constructed, purified pGEXMtDCL1pepA plasmid was selected.

A ready plasmid was used to transform the competent cells of *E. coli* BL21 strain (expressive strain) in order to carry out a procedure of a protein expression 5 µl of purified pGEXMtDCL1pepA plasmid (2ng/µl) were added to 50 µl of competent cells preparation, then gently mixed and incubated at 4° C. for 30 min. Then the bacteria were subjected to thermal shock by incubating the suspension at 42° C. for 30 sec. and rapid cooling at 4° C. 250 µl SOC medium was added to the suspension and shaken for one hour at 37° C. at a speed of 225 rpm, then the suspension was spread onto two petri dishes with a solid LB medium containing ampicillin. The petri dishes were incubated for 16 h at 37° C. From among the colonies obtained on petri dishes was selected one, which was used to initiate the expressive culture. The colony was transferred to 10 ml of liquid LB medium containing ampicillin, culture was shaken for 16 h at 37° C. at 300 rpm and used to inoculate 1000 ml of fresh LB medium with ampicillin. Further incubation was performed under identical culture conditions. Culture's temperature was lowered to 18° C. and expression was induced by adding a solution of isopropyl-β-D-1-thiogalactopyranoside (IPTG) to a final concentration of 0.05 mM once the bacterial suspension reached the optical density $OD_{600}$~0.7. The expression was carried out over the next 16 hours. Bacterial suspension was then centrifuged at 5000 rpm at 4° C. for 15 min, the solution was decanted and the bacterial precipitate was used for isolation of protein.

Extraction of total soluble protein fraction from the bacteria was carried out to isolate the recombinant MtDCL1pepA protein. The bacterial precipitate was suspended in extraction buffer (140 mM NaCl, 2.7 mM KCl, 10 mM $Na_2HPO_4$, 1.8 mM $KH_2PO$, 5 mM DTT, 1×CelLytic, 0.1 mg/ml lysozyme, 25 U/ml benzonase, pH 7.3) using a ratio of 5 ml buffer per 1 g of precipitate, shaken at 23° C. for 15 min and centrifuged at 15,000 rpm. The received supernatant containing the soluble fraction of bacterial proteins was analysed on 10% denaturing polyacrylamide gel (SDS-PAGE). FIG. 6 shows the result of the analysis. MtDCL1pepA was isolated from the supernatant by affinity chromatography of glutathione. The supernatant was applied to a column containing 1 ml of the packed Glutathione Sepharose 4 Fast Flow medium prepared according to manufacturer's description. The medium was washed successively with 10 ml of binding buffer (140 mM NaCl, 2.7 mM KCl, 10 mM Na$_2$HPO$_4$, 1.8 mM KH$_2$PO$_4$, pH 7.3) and 10 ml of buffer for cutting with protease PreScission (50 mM Tris-HCl, 150 mM NaCl, 1 mM EDTA, 1 mM DTT, pH 7.5) and then mixed with 1 ml of buffer for cutting with protease with PreScission protease (40 U/ml) and incubated at 4° C. for 16 hours. The protein was eluted from the column with 1 ml of buffer for cutting with protease PreScission, then an exchange of buffer was made for 50 mM Tris-HCl pH 7.5 using a Millipore Amicon Ultra filter—0.510K, according to manufacturer's description. The resulting preparation (1 ml) was analysed on the gel (SDS-PAGE) and using Western-blot technique (FIG. 6).

A standard digestion reaction of a miRNAs precursor (hsa-miR 33a) radiolabeled at the 5' end was carried out to determine the activity of the obtained peptide. An analogous series of digestion reactions was performed for comparison, in which instead of the MtDCL1pepA preparation a commercially available Dicer protein from *G. intestinalis* was used. Reactions were carried out in an optimized commercial buffer attached to a Dicer protein from *G. intestinalis*, and in the case of the MtDCL1pepA peptide additionally in a 20 mM Tris-HCl pH 7.5 with 250 mM NaCl, 2.5 mM MgCl2 buffer. In all cases, the reactant (10 picomoles) was first heated at 85° C. for 3 minutes and then slowly cooled (1° C./min.) to 23° C. in order to obtain the most homogeneous structure of the product. An appropriate buffer and enzyme were added to the substrate's solution (MtDCL1pepA preparation—7 µl, Dicer—according to manufacturer's description) after cooling. The reaction was carried for 16 hours at 37° C. The analysis of reaction products was performed by electrophoresis on 12% denaturing polyacrylamide gel (FIG. 6). A number of products were obtained in the reaction with the MtDCL1pepA peptide, most of which are in the range of 20-25 nucleotides in length, which corresponds to the length of short regulatory RNAs. The reaction with the Dicer protein from *G. intestinalis* definitely gives a different set of products, from which two main (36 and 37 nucleotides in length) are much longer than the typical regulatory RNA (comparison, see FIG. 6).

The above-described preliminary activity tests showed that the resulting MtDCL1pepA peptide exhibits the expected endoribonuclease activity, catalysing the reaction of cutting short RNA duplexes out of double-stranded miRNA precursor. These products have, as expected, a length of 20-25 nucleotides. This shows that the MtDCL1pepA has a catalytic activity characteristic for Dice-like proteins and can be successfully used for the production of small regulatory RNAs.

LITERATURE

Margis R, Fusaro A F, Smith N A, Curtin S J, Watson J M, Finnegan E J, Waterhouse P M (2006) The evolution and diversification of Dicers in plants. FEBS Lett 580:2442-2450 Science. 2006 Jan. 13; 311(5758):195-8. Structural basis for double-stranded RNA processing by Dicer. Macrae I J, Zhou K, Li F, Repic A, Brooks A N, Cande W Z, Adams P D, Doudna J A.

[x3] *The Pfam protein families database*: R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-22

Sambrook J., Fritsch E., Maniatis T., Molecular Cloning A Laboratory manual, 1989, Second Edit., Cold Spring Harbor Lab. Press, pp. 1.26-1.28.

```
List of sequences

SEQ ID NO: 1
MtDCL1pepA peptide sequence
>MtDCL1pepA
DVVKASGLVPNRDSMETQNHINMTTKGKLMMADTCTSPDDLVGRIVTAA
HSGKRFYVDSIRYEMTAENSFPRKEGYLGPLEYSSYADYYKQKYGVDLA
YKQQPLIRGRGVPYCKNLLSPRFEHSEGHEDETEETHDKTYYVFLPPEL
CLVPPLPGSLVRGAQRLPSIMRRVESMLLAVQLKNMINYPVQASKILEA
LTAASCQETFCYERAELLGDAYLKWVVSRFLFLKHPQKHEGQLTRMRQQ
MVSNMVLYRYALSKGLQSYILADRFAPSRWAAPGVLPVFDEDTKDEESS
LFDQERSIFKAERMDNTDEFEDEMEDGELESDSSSYRVLSSKTLADVVE
ALIGVYYVEGGKNAANHLMKWIGIHIEIDPDEMECITRPSNVPDSILRS
VDFDALEGALNIKFKDKGLLIESITHASRPSSGVSCYQRLEFVGDAVLD
HLITRHLFFSYTDLPPGRLTDLRAAAVNNENFARVTVKHNLHLHLRHGS
SALEKQIKDFVREVQDELSKPGFNSFGLGDCKAPKVLGDILESIAGAIF
LDSGRNTAVVWKVFQPLLHPMVTPETLPMHPVRELQERCQQQAEGLEYR
ASRAGNLATVEVFIDGVQVGAAQNPQKKMAQKLAARNALAALKEKEESK
IQEKNDEKETKSGNQTFTRQTLNDICLRRNWPMPFYRCVSEGGPAHAKK
FTFAVRVNTTDKGWTDECVGEPMPSVKKAKDSAAVLLLELINKLYSS SEQ ID NO: 2
J08-10 oligomer
TAGAATAGGCGTTGATACACAGCAATAGG SEQ ID NO: 3
J08-13 oligomer
ACAACCACTGCTTGCTTCTGATTGG

SEQ ID NO: 4
FWD
CCGAATTCCGATGTAGTGAAAGCTTCAGGATTG

SEQ ID NO: 5
REV1
GTGAGCCTTGTCATCGTCGTCCTTGTAGTCTGACCACTATAATTTGTTT
ATTAGTTCC

SEQ ID NO: 6
REV2
GTAGTCGACTCAGTGTTTGTGACGGTGGTTGTGAGCCTTGTCATCGTCG
T
```

The invention claimed is:

1. A peptide comprising: an amino acid sequence as shown in SEQ ID NO: 1, wherein the peptide exhibits an enzymatic activity of a Dicer-like protein.

2. The peptide according to claim 1, wherein said peptide is produced in a prokaryotic or eukaryotic system.

3. The peptide according to claim 1, wherein said peptide cleaves a double-stranded RNA (dsRNA) substrate, thereby producing short RNA products.

4. A method of using the peptide according to claim 1, wherein said method comprises: the peptide cleaving a double stranded RNA (dsRNA) substrate to generate short 15-30 nucleotide RNA molecules.

* * * * *